United States Patent [19]

Wiley

[11] 4,358,590
[45] Nov. 9, 1982

[54] 6-CARBOXY- AND 6-(ω-CARBOXYALKYL)-3-MERCAPTO-4-AMINO-1,2,4-TRIAZIN-5(4H)-ONES

[76] Inventor: Richard H. Wiley, 8 Roosevelt Cir., Palo Alto, Calif. 94306

[21] Appl. No.: 238,480

[22] Filed: Feb. 26, 1981

[51] Int. Cl.³ .................................... C07D 253/06
[52] U.S. Cl. ............................................. 544/182
[58] Field of Search ................................. 544/182

[56] References Cited

U.S. PATENT DOCUMENTS

| | | | |
|---|---|---|---|
| 4,036,632 | 7/1977 | Westphal et al. | 71/93 |
| 4,058,525 | 11/1977 | Hofer et al. | 544/182 |
| 4,252,944 | 2/1981 | Wiley | 544/182 |

*Primary Examiner*—John M. Ford

[57] ABSTRACT

The title compounds are prepared by the reaction of thiocarbonohydrazide with α-ketodicarboxylic acids and characterized. They show plant growth regulatory activity.

6 Claims, No Drawings

6-CARBOXY- AND 6-(ω-CARBOXYALKYL)-3-MERCAPTO-4-AMINO-1,2,4-TRIAZIN-5(4H)-ONES

BACKGROUND

6-Alkyl and aryl)-3-mercapto-4-amino-1,2,4-triazinones are known and, with their various derivatives, are an important class of herbicides (U.S. Pat. No. 3,966,715; Chem. Ber. 97, 2173 (1964). Such triazinones are customarily prepared by the reaction of thiocarbohydrazide with α-ketoacids in neutral solutions at 90°–100° C. Neither 6-carboxy- nor any 6-(ω-carboxyalkyl), i.e. 6-HOOC(CH$_2$)$_n$-, triazinone has been prepared by this process nor have any such compounds been described in the literature. It is noted that 6-carbalkoxyalkyl (i.e., ROOCCH$_2$—) esters have been described as has also the uniquely sterically hindered and thus unreactive 6-(o-carboxyphenyl) derivative (U.S. Pat. No. 4,252,944). It is also known that some of the α-ketodicarboxylic acid reactants required for the preparation of the products of this invention are easily decarboxylated and base sensitive and would not survive the previously described techniques and conditions used for the preparation of triazinones.

DESCRIPTION OF THE INVENTION

α-Ketoalkane-α, -dicarboxylic acids are reacted with thiocarbohydrazide at 50°–70° C. with or without added mineral acid to give crystalline 6-(ω-carboxyalkyl-3-mercapto-4-amino-1,2,4-triazin-5-ones and their 6-carboxy parent analog.

The α-ketoalkane-α, ω-dicarboxylic acids used in the preparation of the products of this invention are α-ketomalonic (in its hydrated form), α-ketosuccinic acid, α-ketoglutaric acid, and α-ketoadipic acid. All of these acids are available by known processes or are available from chemical suppliers. Other α-ketoalkane-α,ω-dicarboxylic acids are available by known synthetic reactions and are operable in this invention. Thiocarbohydrazide is also available from chemical suppliers. The materials as supplied are usually sufficiently pure for use as supplied but since all are subject to deterioration and decomposition on storage, they are purified by recrystallization, if such deterioration is obvious or extensive, prior to use.

The products of this invention are useful themselves as herbicides and pesticides of the triazinone type such as metribuzin (Merck Index No. 6027) and in the preparation of related derivatives of known types (aldimines; 3-alkylthio-; N-acyl). They are also useful as antimetabolites and metabolites by virtue of their involvement in ketoglutaric acid and related transaminase reactions in the citric acid cycle.

The following examples give specific illustrations of the procedures used in the preparation of the products of this invention.

EXAMPLE 1

A solution of 1.0 g of thiocarbohydrazide in 20 ml of water to which has been added 1 ml of conc. hydrochloric acid is prepared and warmed to 70° C. To this is added 1.5 g of α-ketoglutaric acid and the mixture warmed and stirred to solution. On standing at room temperature the product-6-(2'-carboxyethyl)-3-mercapto-4-amino-1,2,4-triazin-5-one-separates as platelets, mp 195°–200° C. with decomposition. Yield 1.95 g. Anal. (vacuum dried over phosphorus petoxide): Calcd. for C$_6$H$_8$O$_3$N$_4$S: C, 33.33; H, 3.70; N, 25.92; neutr. equiv. 216/108. Found: C, 33.22; H, 3.82; N, 25.82; neutr. equiv. 218/108.5. The potentiometric titration shows breaks at pH 9.0 and 6.0 characteristic of two weakly basic acidic groups (i.e., COOH and SH).

EXAMPLE 2

Example 1 is repeated at 90° C. There is some decomposition as evidenced by gas evolution. The same product is obtained but in a white crystalline formand in a yield of 0.9 g, mp 195°–200° C. with decomposition. Neutr. equiv.: Found: 209/103.

EXAMPLE 3

Example 1 is repeated at 50° C. α The same product is formed but is contaminated with unreacted starting material.

EXAMPLE 4

Example 1 is repeated without the added hydrochloric acid. The same product is obtained but in a slightly more yellow color.

EXAMPLE 5

Example 1 is repeated using 1.0 g of thiocarbohydrazide in 20 ml of water with one ml of conc. hydrochloric acid and 1.8 g of ketomalonic acid hydrate in 15 ml of water with 3 ml of conc. hydrochloric acid. On mixing the reactants at 60°–65° C. a yellow color forms and the product, a mixture of 6-carboxy-3-mercapto-4-amino-1,2,4-triazin-5-one and its hydrate, precipitates. During this reaction there is decomposition as evidenced by gas evolution. At the onset of such gas evolution the reaction mixture is immediately cooled in ice. The yield of product is 0.8 g, mp 160°–200° C. depending on the rate of heating; resolidifies and remelts at 225°–230° C. The vacuum dried product gives analytical values indicating that it is a mixture of 30% of the triazinone and 70% of its hydrate presumably present as the uncyclisized hydrazide or as the triazinone hydrated at the 5-position. Anal.: Cald. for C$_4$H$_6$O$_3$N$_4$S.0.7H$_2$O: C, 25.84; H, 2.66; N, 27.96; neutr. equiv., 203,101.5. Found: C, 24.05; H, 2.64; N, 27.91; neutr. equiv., 198, 99. Without hydrochloric acid there is greater loss due to decarboxylation. At over 65° C. there is extensive decarboxylation.

EXAMPLE 6

Example 1 is repeated using 107 mg of α-ketoadipic acid in 1.5 ml of water and 66 mg of thiocarbohydrazide in 0.5 ml of water with 0.7 ml of conc. hydrochloric acid. The solutions are mixed with 45°–50° C. and warmed to 70° C. at which temperature a clear solution results. This solution is cooled slowly to room temperature. On standing about one hour crystals of the product, 6-(3'-carboxypropyl)3-mercapto-4-amino-1,2,4-triazin-5-one form. These are collected and dried at 55° C./0.5 mm. Anal. Calcd. for C$_7$H$_{10}$O$_3$N$_4$S: neutr. equiv., 232.0, 116. Found: neutr. equiv., 229.7, 113. The product melts at 143°–6° C.

EXAMPLE 7

To a solution of 424 mg of thiocarbohydrazide in 8 ml of water with 0.2 ml of conc. hydrochloric acid at 50° C. is added 500 mg of oxaloacetic acid (α-ketosuccinic acid). The solution is warmed gently to 60° C. to obtain a clear solution whereupon decarboxylation sets in. The mixture is immediately cooled to ice temperature whereupon crystals form. The crystals are collected, vacuum dried, and titrated. Additional product separates from the mother liquor on standing. The yield of product is from the first crop of crystals is 0.3 g; from the second, 0.4 g. The product is 6-carboxymethyl-3-mercapto-4-amino-1,2,4-triazin-5-one, mp 205°–6° C. Anal. Calcd. for $C_5H_6N_4O_3S$: neutr. equiv. 202, 101. Found: neutr. equiv. 199.2, 99.2.

I claim:

1. 6-ω-Carboxyalkyl)-3-mercapto-4-amino-1,2,4-triazin-5-ones in which the ω-carboxyalkyl group has the formula $HOOC(CH_2)_n$-with n having a value of one to four.

2. A 6-substituted-3-mercapto-4-amino-1,2,4-triazin-5-one in which the 6-substituent is carboxy-, carboxymethyl-, 2-carboxyethyl-, 3-carboxypropyl-, or 4-carboxybutyl.

3. 6-Carboxy-3-mercapto-4-amino-1,2,4-triazin-5-one.

4. 6-Carboxymethyl-3-mercapto-4-amino-1,2,4-triazin-5-one.

5. 6-(2'-Carboxyethyl)-3-mercapto-4-amino-1,2,4-triazin-5-one.

6. 6-(3'-Carboxypropyl)-3-mercapto-4-amino-1,2,4-triazin-5-one.

* * * * *